(12) United States Patent
Bansal et al.

(10) Patent No.: US 11,298,010 B2
(45) Date of Patent: Apr. 12, 2022

(54) IMAGING AND COLLECTION DEVICE AND RELATED SYSTEMS AND METHODS

(71) Applicants: University of Kansas, Lawrence, KS (US); The United States Government as Represented by the Department of Veterans Affairs, Washington, DC (US)

(72) Inventors: Ajay Bansal, Mission Hill, KS (US); Lane Christenson, Leawood, KS (US); Nick Baker, Horseshoe Bay, TX (US); Ryan Baskins, Katy, TX (US); John Stark, Lawrence, KS (US); Nourouddin Sharifi, Schenectady, NY (US); Hadi Kh A Kh Alzuabi, Ardiya (KW); Parker Gill, Overland Park, KS (US)

(73) Assignees: University of Kansas, Lawrence, KS (US); Department of Veterans Affairs, Washington, DC (US)

( * ) Notice: Subject to any disclaimer, the term of this patent is extended or adjusted under 35 U.S.C. 154(b) by 156 days.

(21) Appl. No.: 16/481,541

(22) PCT Filed: Jan. 31, 2018

(86) PCT No.: PCT/US2018/016174
§ 371 (c)(1),
(2) Date: Jul. 29, 2019

(87) PCT Pub. No.: WO2018/144562
PCT Pub. Date: Aug. 9, 2018

(65) Prior Publication Data
US 2019/0387961 A1 Dec. 26, 2019

Related U.S. Application Data

(60) Provisional application No. 62/452,539, filed on Jan. 31, 2017.

(51) Int. Cl.
*A61B 1/04* (2006.01)
*A61B 1/00* (2006.01)
(Continued)

(52) U.S. Cl.
CPC .......... *A61B 1/041* (2013.01); *A61B 1/00082* (2013.01); *A61B 1/00087* (2013.01);
(Continued)

(58) Field of Classification Search
CPC . A61B 1/041; A61B 1/00082; A61B 1/00087; A61B 1/00133
See application file for complete search history.

(56) References Cited

U.S. PATENT DOCUMENTS

2007/0161851 A1  7/2007  Takizawa et al.
2008/0199065 A1*  8/2008  Swain ................ A61B 1/00156
                                                      382/133
(Continued)

*Primary Examiner* — Aaron B Fairchild
(74) *Attorney, Agent, or Firm* — Sean Solberg

(57) ABSTRACT

Disclosed herein are devices having both imaging components and cell collection apparatuses. More specifically, the various embodiments disclosed herein include swallowable capsules having deployable collection structures, expansion structures to deploy the collection structures, and imaging components.

20 Claims, 11 Drawing Sheets

(51) Int. Cl.
*A61B 5/00* (2006.01)
*A61B 10/00* (2006.01)
*A61B 10/02* (2006.01)

(52) U.S. Cl.
CPC ...... *A61B 1/00094* (2013.01); *A61B 1/00133* (2013.01); *A61B 5/6861* (2013.01); *A61B 10/0096* (2013.01); *A61B 2010/0216* (2013.01)

(56) References Cited

U.S. PATENT DOCUMENTS

2009/0253999 A1 10/2009 Aoki et al.
2011/0166416 A1 7/2011 Katayama et al.

\* cited by examiner

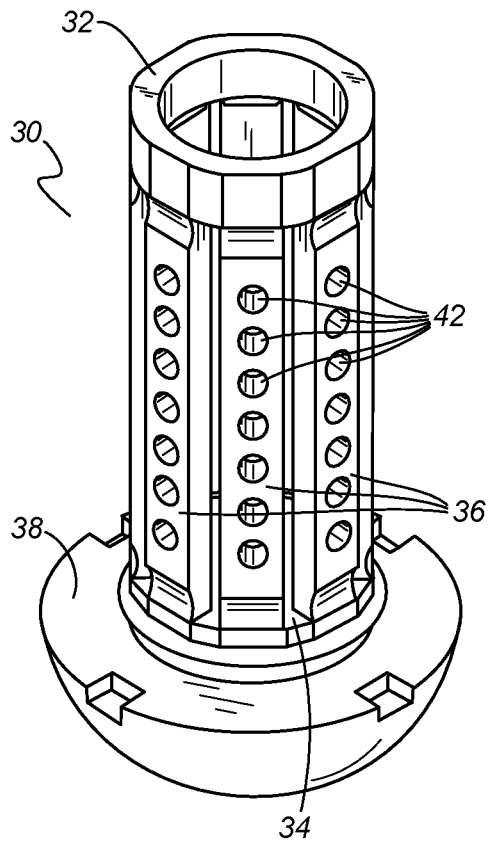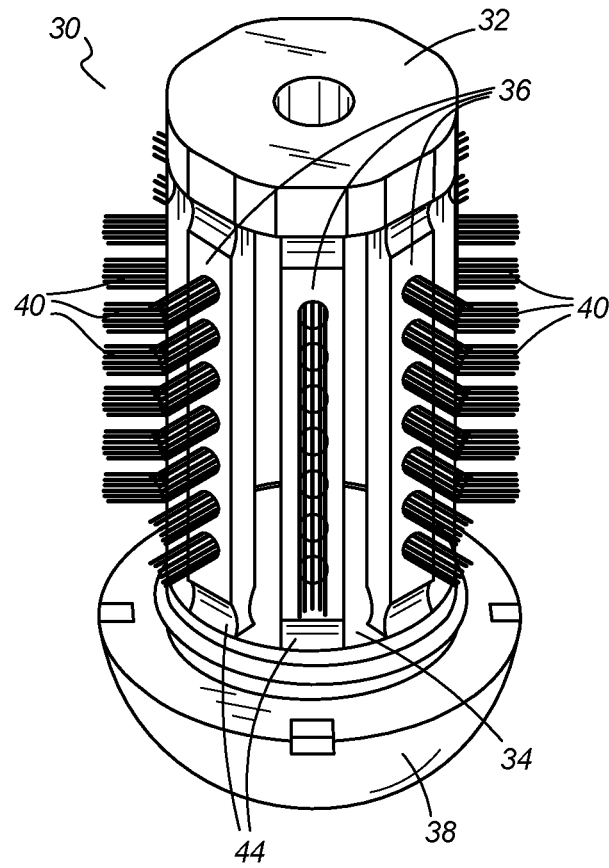
FIG. 2A  FIG. 2B
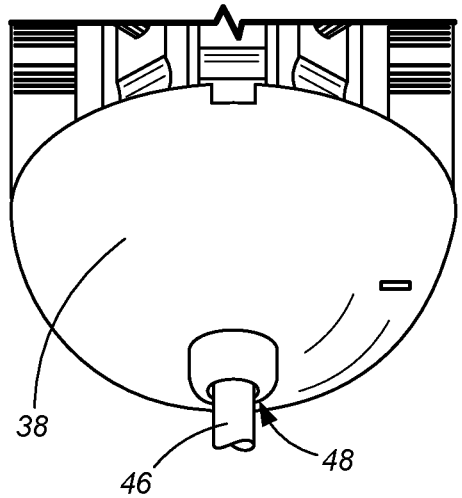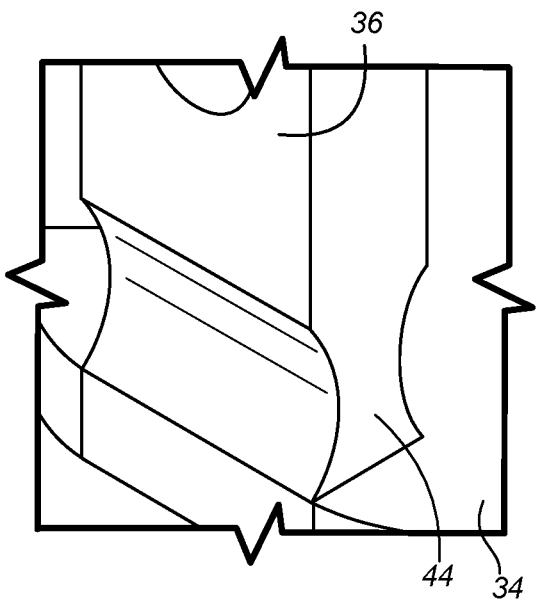
FIG. 2C  FIG. 2D

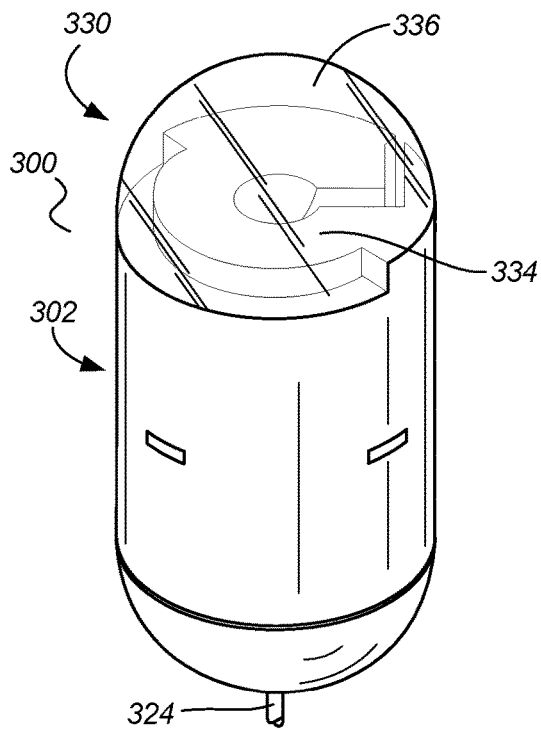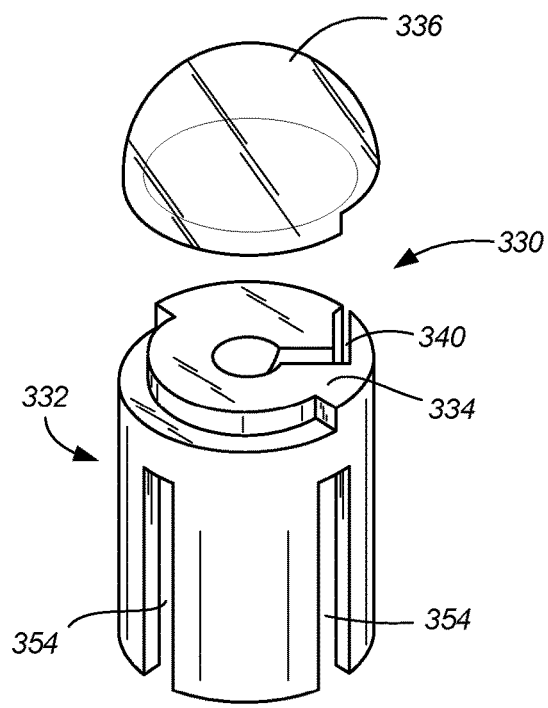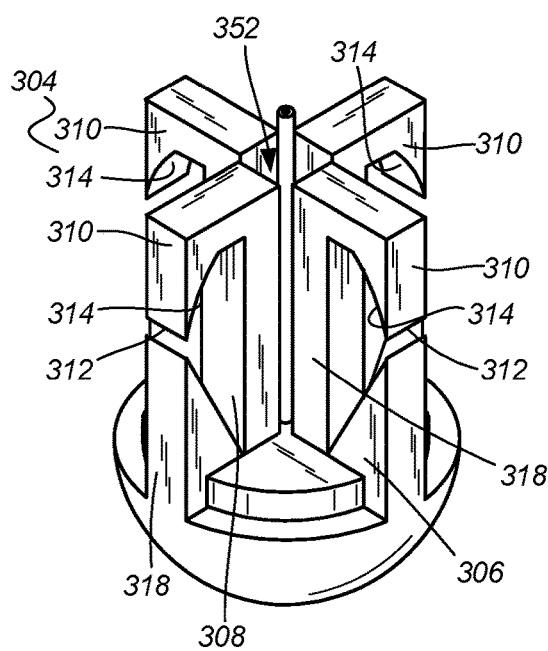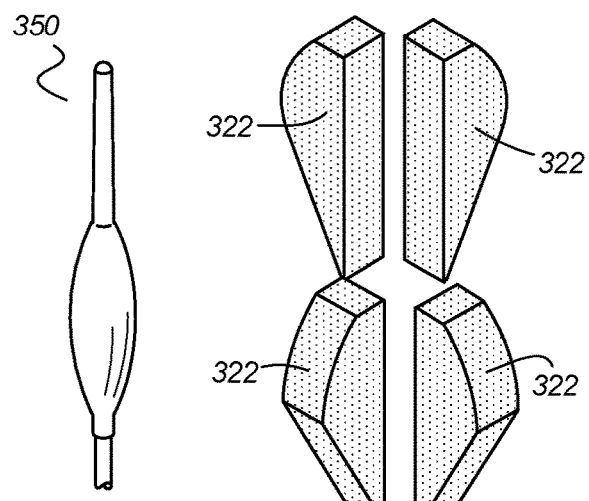
FIG. 7A
FIG. 7B
FIG. 7C
FIG. 7D
FIG. 7E

IMAGING AND COLLECTION DEVICE AND RELATED SYSTEMS AND METHODS

CROSS-REFERENCE TO RELATED APPLICATION(S)

This application claims priority to International PCT Application No. PCT/US18/16174, filed on Jan. 31, 2018, which claims the benefit under 35 U.S.C. § 119(e) to U.S. Provisional Application 62/452,539, filed Jan. 31, 2017 and entitled "Imaging and Collection Device and Related Systems and Methods," which is hereby incorporated herein by reference in its entirety.

FIELD OF THE INVENTION

The various embodiments herein relate to diagnostic devices for esophageal conditions, and more specifically to swallowable devices having dual imaging and tissue/cell collection functionalities.

BACKGROUND OF THE INVENTION

Esophageal cancer is the sixth most common cause of cancer-related death in the world and has increased by six-fold over the past decade. Esophageal cancer and related precancerous conditions such as Barret's esophagus are difficult to diagnose. Early diagnosis is especially important. Esophogeal cancer results in an 80% mortality rate after 5 years, and the majority of the population with precancerous conditions are undiagnosed. However, studies suggest that esophageal cancer is curable with improvement in survival rates if diagnosed in time. Also, another relevant cancer closely related to esophageal cancer is a cancer of the cardia, the most proximal portion of the stomach. This cancer is also increasing at a fast pace and has poor survival that can be improved with early diagnosis. Other related diseases include, for example, eosinophilic esophagitis, which is an allergic disorder of the esophagus that is rapidly increasing in incidence in the United States and often requires multiple endoscopies each year during treatment.

Current diagnostic approaches are endoscopic techniques that involve cytological forceps, brushes, or sponges that are attachments to or extend from the distal end of an endoscope. These processes are invasive and expensive, requiring an endoscopic specialist to perform the procedure on a sedated patient.

Some newer technologies use pill-sized cameras, but the collection capabilities of those devices are poor or ineffective in practice.

There is a need in the art for an improved method, system, and device for both the imaging of a patient's esophagus and/or stomach and the collection of stomach and/or esophageal cells.

BRIEF SUMMARY OF THE INVENTION

Discussed herein are various device embodiments and related methods for imaging and collecting tissue in the esophagus and/or stomach of a patient.

In Example 1, a swallowable capsule comprises a core component, an expansion component disposed within the core component, an outer casing comprising a plurality of openings, and an imaging component disposed on the capsule. The core component comprises a plurality of deployment structures operably coupled to the core component and at least one collection structure coupled to each of the plurality of deployment structures. The deployment structures are configured to move between an undeployed configuration and a deployed configuration. Expansion of the expansion component urges the plurality of deployment structures toward the deployed configuration. The plurality of openings correspond to the plurality of deployment structures, wherein the plurality of openings are configured to receive the at least one collection structures when the deployment structures are disposed in the deployed configuration such that the at least one collection structures protrude out of the openings.

Example 2 relates to the swallowable capsule according to Example 1, wherein the deployment structures are deployment struts or deployment rods.

Example 3 relates to the swallowable capsule according to Example 1, wherein the at least one collection structure is coupled to each of the plurality of deployment structures such that the at least one collection structure extends radially outward from the deployment structure.

Example 4 relates to the swallowable capsule according to Example 1, wherein the expansion component is an inflatable balloon.

Example 5 relates to the swallowable capsule according to Example 1, further comprising a transparent shell disposed at a distal end of the capsule, wherein the imaging component is disposed therein.

Example 6 relates to the swallowable capsule according to Example 1, wherein the at least one collection structure comprises a brush or a collection member comprising an opening.

Example 7 relates to the swallowable capsule according to Example 1, wherein each of the plurality of deployment structures is coupled at a proximal end to the core component.

Example 8 relates to the swallowable capsule according to Example 1, wherein each of the plurality of deployment structures is coupled at each end to the core component.

In Example 9, a swallowable capsule comprises a capsule body comprising an outer casing, a plurality of deployment structures disposed within the body, wherein the deployment structures are configured to move between an undeployed configuration and a deployed configuration, at least one collection structure coupled to each of the plurality of deployment structures, a plurality of openings defined in the outer casing, wherein the plurality of openings correspond to the plurality of deployment structures, wherein the plurality of openings are configured to receive the at least one collection structures when the deployment structures are disposed in the deployed configuration such that the at least one collection structures protrude out of the openings, an expansion component disposed within the capsule body adjacent to the plurality of deployment structures, wherein expansion of the expansion component causes the plurality of deployment structures to move toward the deployed configuration, and an imaging component disposed on the capsule body.

Example 10 relates to the swallowable capsule according to Example 9, wherein each of the plurality of deployment structures is coupled at a proximal end to an interior portion of the capsule body.

Example 11 relates to the swallowable capsule according to Example 10, wherein the at least one collection structure is disposed at a distal end of each of the plurality of deployment structures.

Example 12 relates to the swallowable capsule according to Example 9, wherein the at least one collection structure comprises a blade.

Example 13 relates to the swallowable capsule according to Example 9, further comprising at least one porous insert positioned adjacent to the at least one collection structure.

Example 14 relates to the swallowable capsule according to Example 9, wherein the at least one collection structure is coupled to each of the plurality of deployment structures such that the at least one collection structure extends radially outward from the deployment structure.

Example 15 relates to the swallowable capsule according to Example 9, wherein the expansion component is an inflatable balloon.

In Example 16, a method of diagnosing a condition of the esophagus or the stomach of a patient comprises positioning a swallowable capsule in the esophagus or stomach of the patient, collecting cells with the swallowable capsule by expanding the expansion component and thereby urge the plurality of deployment structures into a deployed configuration such that each of the at least one collection structure protrudes through one of the plurality of openings and contacts a target tissue, and removing the swallowable capsule from the patient. The swallowable capsule comprises a capsule body comprising an outer casing, a plurality of deployment structures disposed within the body, at least one collection structure coupled to each of the plurality of deployment structures, a plurality of openings defined in the outer casing, wherein the plurality of openings correspond to the plurality of deployment structures, an expansion component disposed within the capsule body adjacent to the plurality of deployment structures, and an imaging component disposed on the capsule body.

Example 17 relates to the method according to Example 16, further comprising testing the cells to detect the condition after removing the swallowable capsule from the patient.

Example 18 relates to the method according to Example 16, further comprising retracting the at least one collection structure by causing the expansion structure to contract and thereby causing the plurality of deployment structures to retract after collecting cells.

Example 19 relates to the method according to Example 16, wherein the at least one collection structure comprises a brush, a collection member comprising an opening, or a collection member comprising a blade.

Example 20 relates to the method according to Example 16, further comprising capturing images with the imaging component.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2A is a perspective view of an inner component of an imaging and collection device, according to one embodiment.

FIG. 2B is a perspective view of the inner component of FIG. 2A.

FIG. 2C is a perspective view of the proximal cap of the inner component of FIG. 2A.

FIG. 2D is an expanded view of a portion of the inner component of FIG. 2A.

FIG. 7A is a perspective view of an imaging and collection device, according to yet another embodiment.

FIG. 7B is a perspective view of an outer shell and transparent cover, according to one embodiment.

FIG. 7C is a perspective view of an inner component, according to one embodiment.

FIG. 7D is a side view of an inflation component, according to one embodiment.

FIG. 7E is a perspective view of porous inserts, according to one embodiment.

DETAILED DESCRIPTION

The various embodiments disclosed or contemplated herein relate to methods, systems, and devices for the imaging of a patient's esophagus and/or stomach and the collection of esophageal and/or stomach cells. In some examples, the dual-function imaging and collection device can be used for the diagnosis and/or treatment of certain diseases. The use of the device for early diagnosis can result in early detection and potentially successful treatment of esophageal or stomach ailments as discussed herein, including cancer.

As discussed above, the various device embodiments herein can be used for the diagnosis of a variety of diseases and conditions, including, for example, esophageal cancer, various pre-cancerous conditions including Barret's esophagus, cancer of the cardia, and eosinophilic esophagitis. It is understood that the various device implementations can also be used for any other medical purpose relating to the imaging of a patient's esophagus and/or stomach and/or collection of cells therefrom.

Figure 1A:
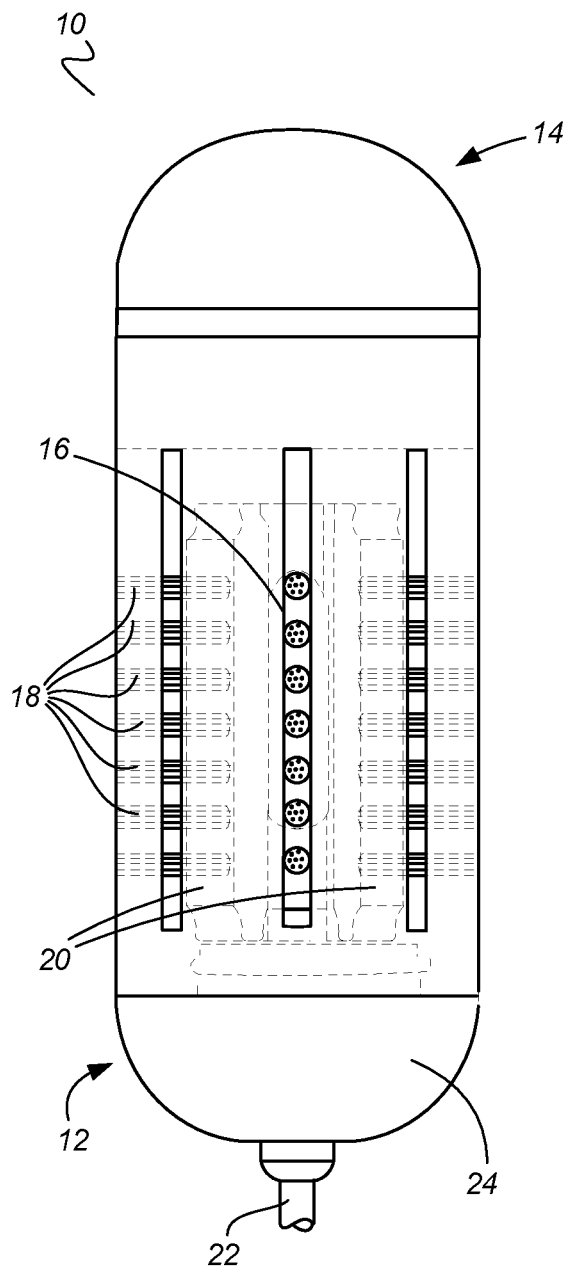
FIG. 1A is a side view of an imaging and collection device, according to one embodiment.
Figure 1B:
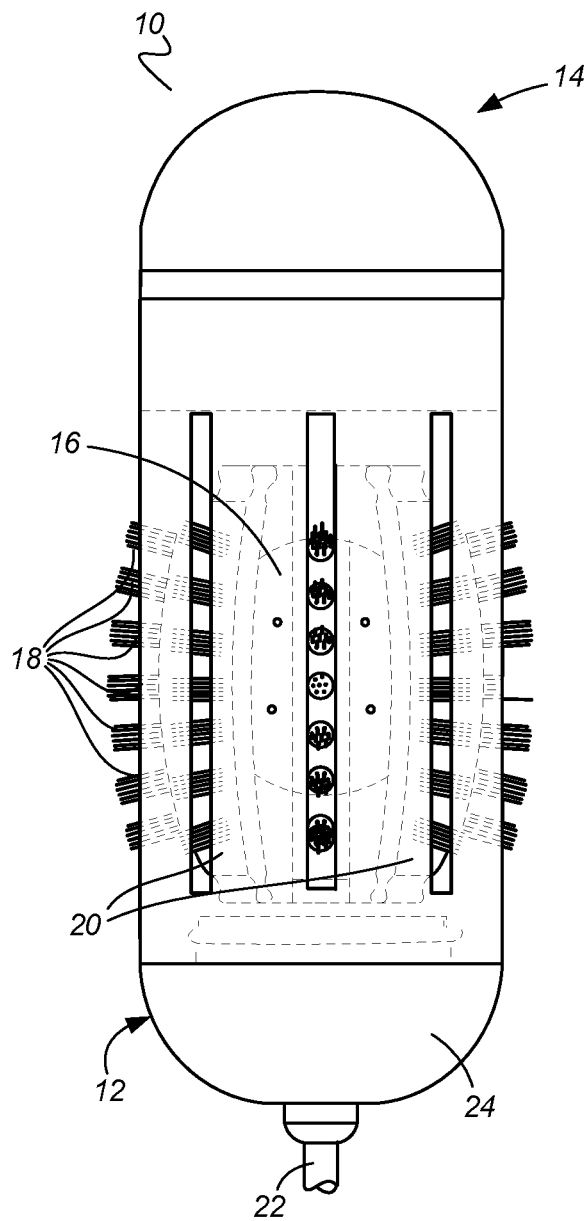
FIG. 1B is a side view of the imaging and collection device of FIG. 1A.

One embodiment of a dual-function imaging and collection device 10 is depicted in FIGS. 1A and 1B. As will be described in further detail below, the device 10 has a body 12, an imaging section 14, an inflatable balloon 16, an array of deployable brushes 18 coupled to brush deployment struts 20, a proximal cap 24, and is coupled at the proximal cap 24 to a catheter tube 22. The device body 12 in this implementation is a capsule 12 or has a capsule-like shape. Alternatively, the device body 12 can have any shape that allows the body 12 to be swallowed and positioned within and through the esophagus and into the stomach of a patient. In use, the deployable bristles 18 can be moved from their undeployed state or position as shown in FIG. 1A to their deployed state or position in FIG. 1B. The deployment of the bristles 18 is achieved via the inflation of the inflatable balloon 16, as will be described in further detail below.

According to one embodiment, the body 12—and any other body embodiments disclosed or contemplated herein—has a diameter ranging from about 6 mm to about 12 mm and a length ranging from about 15 mm to about 30 mm. In one specific example, the body 12 has a diameter of about 10 mm and a length of about 28 mm.

Figure 2E:
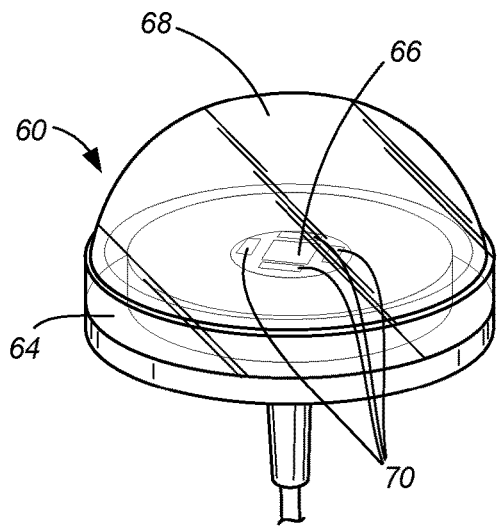
FIG. 2E is a perspective view of an imaging section, according to one embodiment.
Figure 2F:
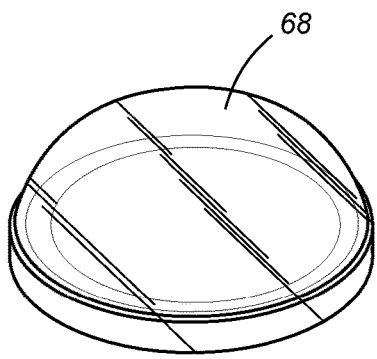
FIG. 2F is a perspective view of the transparent cover of the imaging section of FIG. 2E.
Figure 2G:
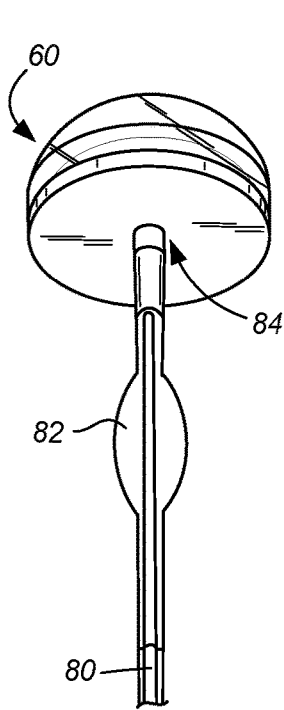
FIG. 2G is a perspective view of a catheter tube coupled to the imaging section of FIG. 2E.
Figure 2H:
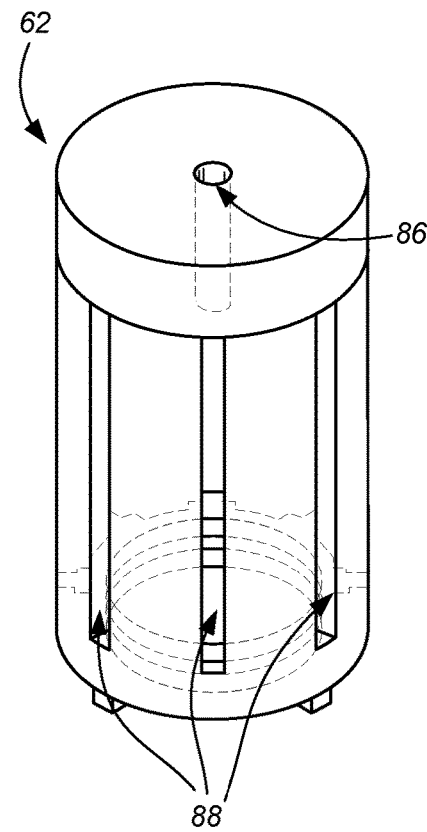
FIG. 2H is a perspective view of an outer shell, according to one embodiment.
Figure 2I:
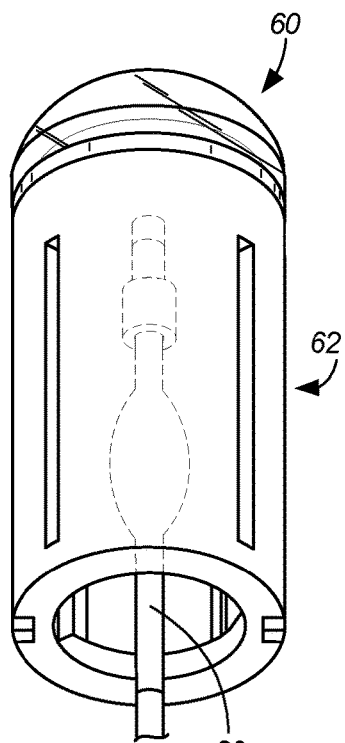
FIG. 2I is a perspective view of the outer shell of FIG. 2H coupled to or integral with the imaging section of FIG. 2E.
Figure 2J:
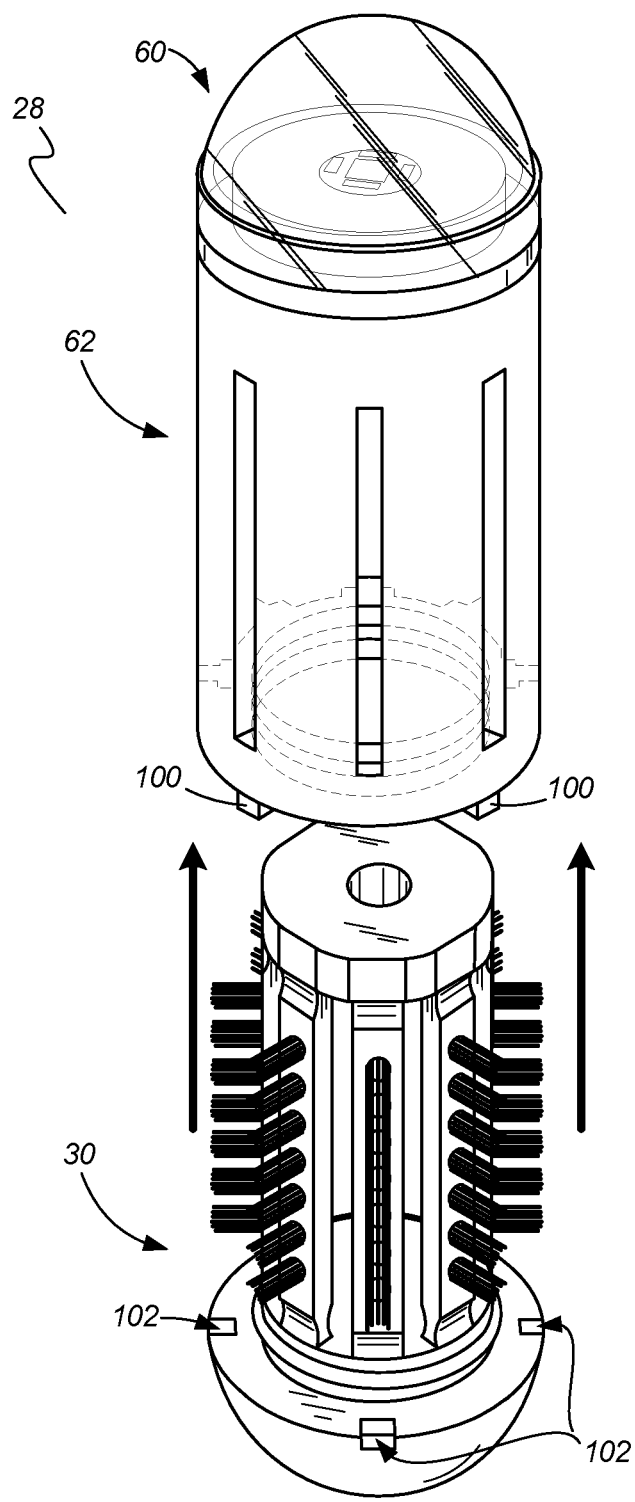
FIG. 2J is a perspective view of the inner component of FIG. 2A being coupled to the outer shell of FIG. 2H.
Figure 2K:
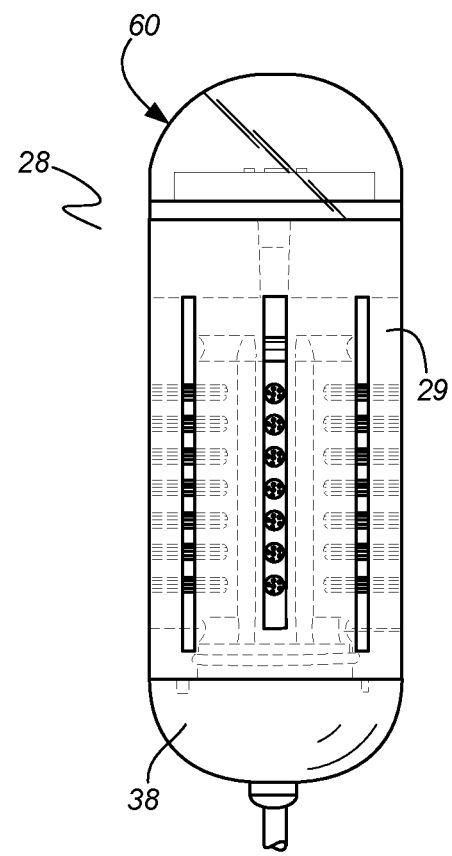
FIG. 2K is a side view of the inner component of FIG. 2A and outer shell of FIG. 2H coupled together.

Another implementation of a dual-function device 28 as best shown in FIGS. 2A-2K has an inner (or core) component 30 that is positioned within the body 29 (as best shown in FIG. 2K) and has a distal ring 32, a proximal ring (or base) 34, a set of brush deployment struts 36 extending between and coupled at each end to the rings 32, 34, and a proximal cap (or end piece) 38 coupled to the proximal base 34. As best shown in FIG. 2B, the struts 36 have several brushes (or bundles of bristles) 40 coupled thereto.

In one embodiment as shown, the inner component 30 has eight struts 36 positioned between and coupled to the rings 32, 34. Alternatively, the number of struts 36 can range from two to ten. In a further alternative, the number of struts 36 can be any number that can be positioned between the rings 32, 34 while having brushes 40 coupled thereto. Each strut 36 in this implementation has seven brushes 40 coupled thereto. Alternatively, the number of brushes 40 can range from one to ten. In a further alternative, the number of brushes 40 can be any number that can be positioned on a strut 36. According to one embodiment, each of the brushes 40 is attached by positioning a proximal end of each brush 40 in an opening 42 defined in the strut 36 (as best shown in FIG. 2A). Alternatively, the brushes 40 can be attached to the struts 36 in any known fashion.

The brushes 40, in accordance with one implementation, can be bundles of bristles. Each of the brushes 40 can have a diameter ranging from about 0.5 to about 1 mm and a length ranging from about 1 to about 3 mm. In one specific embodiment, the brushes 40 have a diameter of about 0.75 mm. The bristles in one specific implementation can be Nylon™ 6.12 bristles each having a diameter of about 0.051 mm. Alternatively, each of the bristles can have a diameter ranging from about 0.025 mm to about 0.075 mm. In one alternative, the brushes are braided wire cytology brushes. In a further embodiment, the brushes can be any known brushes for use in a medical device. It is understood that these characteristics can apply to any brush in any embodiment disclosed or contemplated herein.

Each strut 36 in this specific embodiment is a beam or rib-like structure 36 with a substantially rectangular cross-section. In one embodiment, the struts 36 are made of polypropylene. Alternatively, the struts 36 can be made of any biocompatible polymer having deformable or flexible characteristics. In a further alternative, the struts 36 can be made of any deformable material for a medical device that returns to its original shape/position.

In one embodiment as best shown in FIG. 2D, each strut 36 is coupled to the proximal ring 34 (and the distal ring 32 at the other end of the strut 36 as well) via a hinge 44. In the embodiment as shown, each hinge 44 is a section at each end of each strut 36 that is narrower than the rest of the strut 36. The hinges 44 at both ends of the strut 36 allow for the strut 36 to more easily bend or deform at the hinges 44, thereby resulting in relatively less resistance by each strut 36 as the balloon (such as balloon 16 described above) inflates and urges each strut 36 radially outward in relation to the device body 29. Alternatively, any known mechanical hinge configuration can be used that facilitates bending or deformation of the struts 36 where they are coupled or otherwise attached to the rings 32, 34.

In this implementation, the circular proximal base 34 is coupled directly to the proximal cap 38 as best shown in FIGS. 2A and 2C. Alternatively, the proximal cap 38 can be removably coupled to the proximal base 34 or some other portion of the body 29. The cap 38 can have a round configuration as best shown in FIG. 2C that is part of the capsular shape of the body 29. In this embodiment, a catheter tube 46 (or tube 22 discussed above) is positioned through an opening 48 defined in the cap 38 as best shown in FIG. 2C.

One embodiment of an imaging section 60 and an outer shell 62 is depicted in FIGS. 2E-2I. The imaging section 60, as best shown in FIGS. 2E and 2F, has a base 64, an imaging component 66, and a transparent cover 68 that is disposed over and encloses the imaging component 66. According to certain implementations, the imaging section 60 can also have a lighting component 70. In this specific implementation, the lighting component 70 is a set of four LED nodes 70 that are positioned around the imaging component 66. Alternatively, the lighting component 70 can be any fiber optic or LED lighting component for use in medical devices. In a further alternative, the lighting component 70 can be any known lighting component for use in medical devices. In use, the imaging section 60 allows for the imaging component 66 to capture images of areas distal to the imaging section through the transparent cover 68.

The imaging component 66 (and any other imaging component in any other embodiment disclosed or contemplated herein), according to one embodiment, is a micro-CMOS camera called a NanEye™, which is commercially available from AWAIBA Lda Madeira Tecnopolo, which is based in Funchal, Madeira, Portugal. Alternatively, the imaging component is any CMOS sensor that can be used in a medical device. In a further alternative, the imaging component can be any known camera that can be used in medical devices configured for insertion into a patient.

In one embodiment, the transparent cover 68 is made of ABS plastic. Alternatively, the cover 68 can be made of biocompatible glass or clear polymeric material. In a further alternative, the cover 68 can be made of any biocompatible, substantially transparent material that can be used for medical devices. It is understood that these characteristics can apply to any transparent cover in any embodiment disclosed or contemplated herein.

In one implementation as shown in FIG. 2G, a catheter tube 80 having an inflatable balloon 82 is coupled to the proximal side of the base 64 and extends proximally therefrom such that the balloon 82 is positioned within the outer shell 62 when the shell 62 has been coupled to or is integral with the imaging section 60 as best shown in FIG. 2I. The balloon 82 is in fluid communication with a lumen (not shown) of the tube 80 such that the balloon 82 can be inflated via the tube 80. The tube 80 can be, according to certain embodiments, positioned into or in communication with an opening 84 in the proximal side of the base 64 (through an opening 86 in the outer shell 62 as best shown in FIG. 2H) such that at least one communication line and at least one power line can be coupled to the imaging component 66 through the opening 84.

According to one embodiment, the balloon 82 (and any other balloon in any other embodiment disclosed or contemplated herein) is a medical balloon that has a diameter of about 8 mm and a length of about 7 mm when fully inflated and is commercially available from Vention Medical of South Plainfield, N.J. Alternatively, any balloon in any device embodiment herein can have a diameter when fully inflated ranging from about 6 mm to about 12 mm. In a further alternative, the balloon in any of the implementations herein can be any known balloon for use in medical devices.

The catheter tube 80 (and any tube contemplated herein), in accordance with one embodiment, has an outer diameter ranging from about 0.25 mm to about 2 mm. In one implementation, the tube can have a lumen with a diameter of about 1 mm. The tube 80—and any such tube—is made of polyimide. Alternatively, the tube 80 can be made of any known biocompatible polymer used in medical devices, especially catheters and other types of tubular devices.

The outer shell 62, according to one implementation, can be coupled to or integral with the proximal side of the imaging section 60 as best shown in FIG. 2I to form the outer portion of the device body 29, as best shown in FIG. 2J. The shell 62 in the depicted embodiment has several slots 88 defined therein such that when the shell 62 is disposed over the inner component 30, the brushes 40 and the slots 88 can be aligned such that the brushes 40 extend out of the slots 88 when the brushes 40 are in the deployed position.

In one embodiment, the shell 62 is made of polycarbonate. Alternatively, the shell 62 can be made of any known substantially rigid, biocompatible polymer used in medical devices. In a further alternative, the shell 62 can be made of any substantially rigid material that can be used for medical devices. It is understood that these characteristics can apply to any outer shell in any embodiment disclosed or contemplated herein.

FIG. 2J depicts the positioning of the outer shell 62 over the inner component 30 (or positioning of the inner component 30 within the outer shell 62). In this embodiment, the proximal end of the outer shell 62 has projections 100 that are mateable with the slots 102 defined in the distal edge of the proximal cap 38, thereby coupling the inner component 30 and the outer shell 62 such that neither component rotates in relation to each other when coupled. Further, the projections 100 and slots 102 are positioned such that the coupling of the outer shell 62 and the inner component 30 results in the alignment of the brushes 40 and the slots 88 such that the brushes 40 are deployable through the slots 88.

Alternatively, the device 28 can have a body 29 and no inner component 30. In other words, the body 29 can be a single unitary component having the struts 36 and all other components and features as described above, but without a separate inner component that is separable from and coupleable to the outer shell. Similarly, any of the other device embodiments as disclosed or contemplated herein that are described as having an inner component, including the various additional embodiments described in detail below, can instead have a single, unitary body. Similarly, any device embodiment described as having a single, unitary body component can also alternatively have a separate inner component that is coupleable to an outer shell.

In certain additional alternative implementations, the device 28 can have no imaging component. Further, it is understood that any of the device embodiments disclosed or contemplated herein can have no imaging component.

Figure 3A:
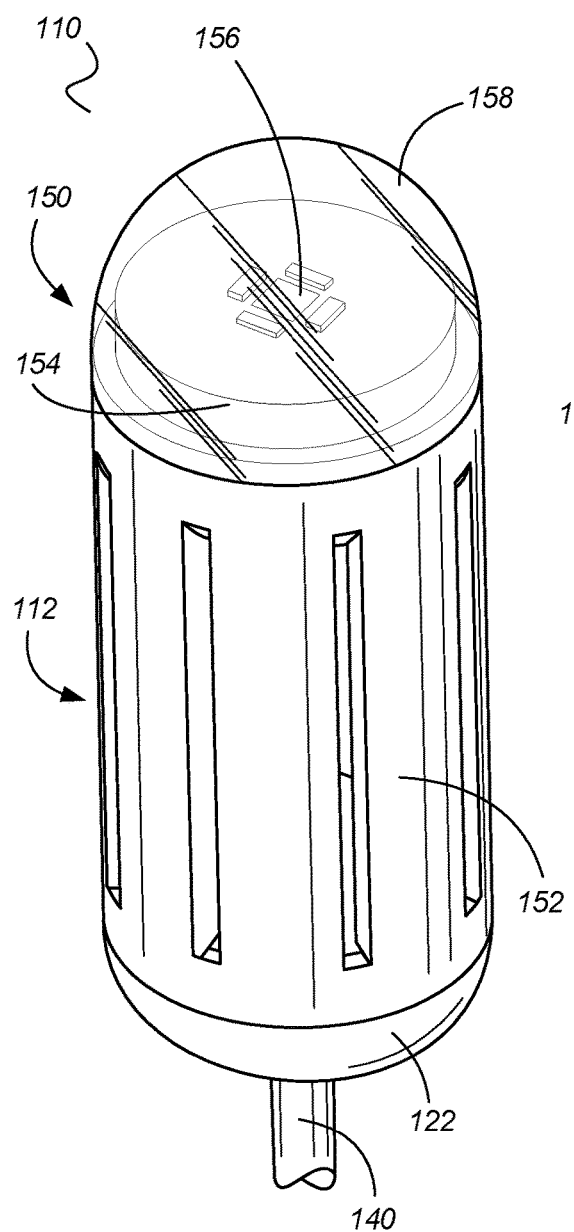
FIG. 3A is a perspective view of an imaging and collection device, according to another embodiment.
Figure 3B:
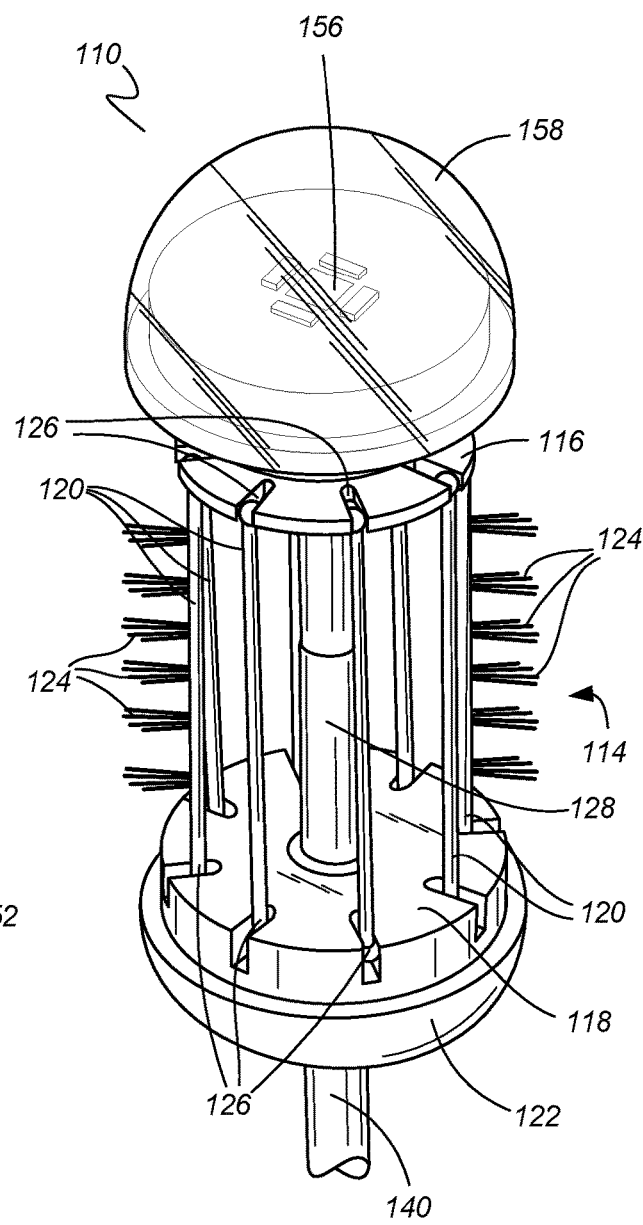
FIG. 3B is a perspective view of the imaging and collection device of FIG. 3A.
Figure 3C:
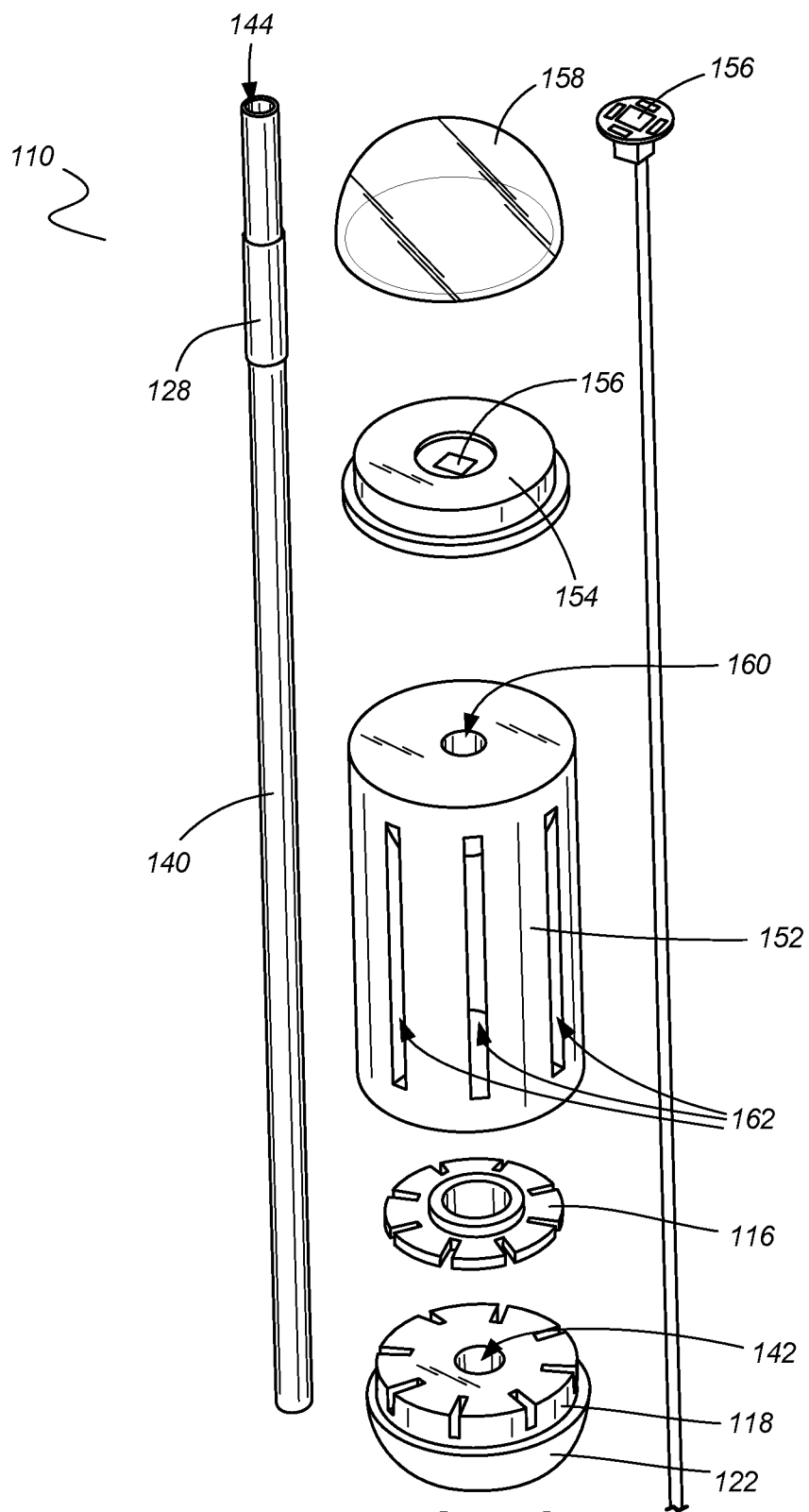
FIG. 3C is an exploded perspective view of the imaging and collection device of FIG. 3A.

Another implementation of a dual-function device 110 is depicted in FIGS. 3A-3C. In this embodiment, the device 110 has an inner (or core) component 114 that is positioned within the body 112 and has a distal ring 116, a proximal ring (or base) 118, a set of brush deployment struts 120 extending between and coupled at each end to the rings 116, 118, and a proximal cap (or end piece) 122 coupled to the proximal base 118. As best shown in FIG. 3B, the struts 120 have several brushes (or bundles of bristles) 124 coupled thereto.

In one embodiment as shown, the inner component 114 has eight struts 120 that are rods 120 positioned between and coupled to the rings 116, 118. Alternatively, the number of rods 120 can range from two to ten. In a further alternative, the number of rods 120 can be any number that can be positioned between the rings 116, 118 while having brushes 124 coupled thereto. Each rod 120 in this implementation has six brushes 124 coupled thereto. Alternatively, the number of brushes 124 can range from one to ten. In a further alternative, the number of brushes 124 can be any number that can be positioned on a rod 120. According to one embodiment, each of the brushes 124 are attached by positioning a proximal end of each brush 124 in an opening (not shown) defined in the rod 120. Alternatively, the brushes 124 can be attached to the rods 120 in any known fashion.

Each strut 120 in this specific embodiment is a rod- or wire-like structure 120 with a substantially circular cross-section. In one embodiment, the rods 120 are made of a flexible, biocompatible polymer. Alternatively, the rods 120 can be made of any deformable or flexible biocompatible material (including, for example, a polymer, metal, or other material) for a medical device that returns to its original shape/position.

In one embodiment as best shown in FIG. 3B, each rod 120 is coupled to the distal and proximal rings 116, 118 via a hinge 126 or other mechanical connection. The hinges 126 at both ends of the rod 120 allow for the rod 120 to more easily bend or deform at the hinges 126, thereby resulting in relatively less resistance by each rod 120 as the balloon 128 discussed below inflates and urges each rod 120 radially outward in relation to the 112. Alternatively, any known mechanical hinge or connection configuration can be used that facilitates bending or deformation of the rods 120 where they are coupled or otherwise attached to the rings 116, 118.

In this implementation, the proximal base 118 is coupled directly to the proximal cap 122 as best shown in FIGS. 3B and 3C. Alternatively, the proximal cap 122 can be removably coupled to the proximal base 118 or some other portion of the body 112. The cap 122 can have a round configuration as best shown in FIG. 3B that is part of the capsular shape of the body 112. In this embodiment, a catheter tube 140 is positioned through an opening 142 defined in the cap 122 and base 118 as best shown in FIG. 3C.

One embodiment of an imaging section 150 and an outer shell 152 is depicted in FIGS. 3A-3C. The imaging section 150 has a base 154, an imaging component 156, and a transparent cover 158 that is disposed over and encloses the imaging component 156. According to certain implementations, the imaging section 150 can also have a lighting component (not shown). In one embodiment, the lighting component (not shown) can be similar to the lighting component 70 discussed above. In use, the imaging section 150 allows for the imaging component 156 to capture images of areas distal to the imaging section 150 through the transparent cover 158.

The catheter tube 140 having an inflatable balloon 128 is coupled to the proximal side of the base 154 and extends proximally therefrom such that the balloon 128 is positioned within the outer shell 152 when the shell 152 has been coupled to or is integral with the imaging section 150. The balloon 128 is in fluid communication with a lumen 144 of the tube 140 (as best shown in FIG. 3C) such that the balloon 128 can be inflated via the tube 140. The tube 140 can be, according to certain embodiments, positioned into or in communication with an opening (not shown) in the proximal side of the base 154 (through an opening 160 in the outer shell 152 as best shown in FIG. 3C) such that at least one communication line and at least one power line can be coupled to the imaging component 156 through the opening (not shown).

The outer shell 152, according to one implementation, can be coupled to or integral with the proximal side of the imaging section 150 as best shown in FIGS. 3A and 3C to form the outer portion of the device body 112, as best shown in FIG. 3A. The shell 152 in the depicted embodiment has several slots 162 defined therein such that when the shell 152 is disposed over the inner component 114, the brushes 124 and the slots 162 can be aligned such that the brushes 124 extend out of the slots 162 when the brushes 124 are in the deployed position.

Figure 4A:
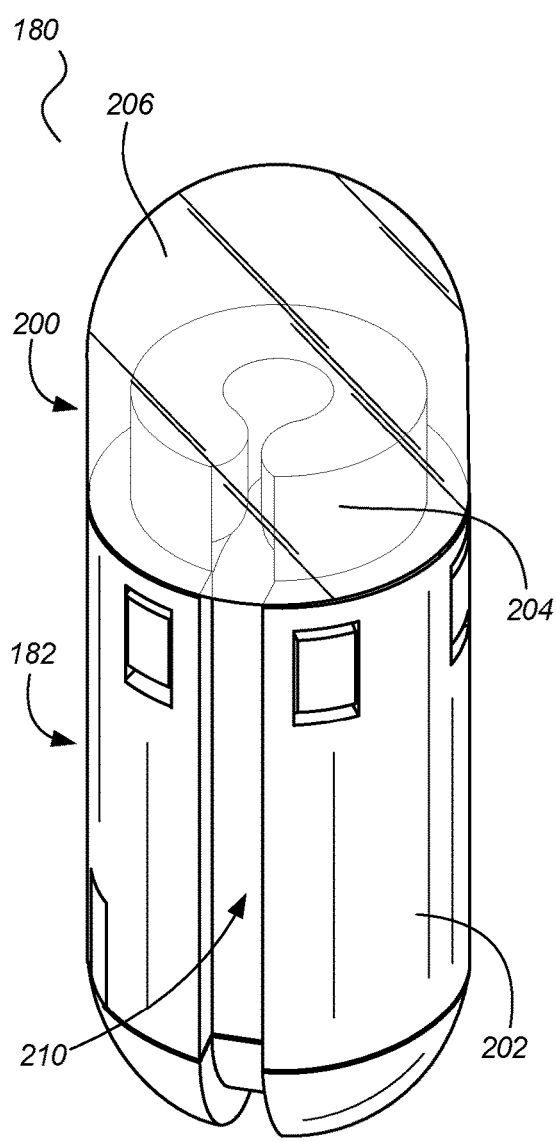
FIG. 4A is a perspective view of an imaging and collection device, according to a further embodiment.
Figure 4B:
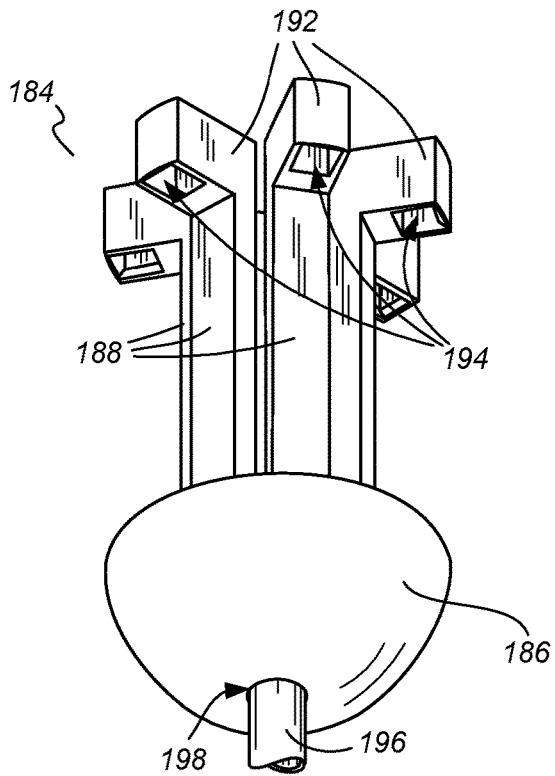
FIG. 4B is a perspective view of the inner component of the device of FIG. 4A.
Figure 4C:
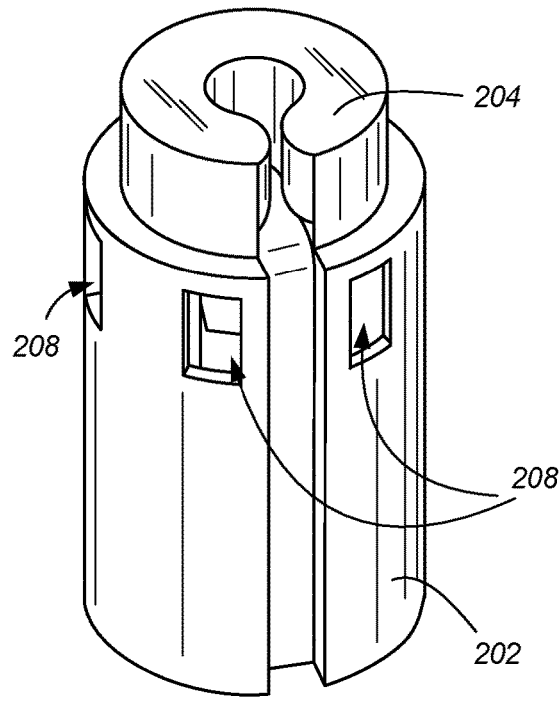
FIG. 4C is a perspective view of the outer shell of the device of FIG. 4A.

Another implementation of a dual-function device 180 is depicted in FIGS. 4A-4C. In this embodiment, the device 180 has an inner (or core) component 184 that is positioned within the body 182 and has a proximal base 186 and a set of collection member deployment struts 188 extending distally from the base 186. As best shown in FIG. 4B, the struts 188 have several collection members 192 coupled thereto.

In one embodiment as best shown in FIG. 4B, the inner component 184 has eight struts 188 (five of which are visible in the figure) coupled to and extending from the proximal base 186. Alternatively, the number of struts 188 can range from two to ten. In a further alternative, the number of struts 188 can be any number that can be coupled to the base 186, while having collection members 192 coupled thereto. In this embodiment, each strut 188 has a collection member 192 instead of one or more brushes. In this implementation, each collection member 192 is a protrusion extending from the strut 188 with an opening 194 defined in the protrusion, thereby allowing for the capture of cells within the opening 194 when the collection members 192 are deployed in a fashion similar to the brushes in other embodiments discussed elsewhere herein. In one embodiment, each collection member 192 is referred to as a "scraper" 192 because it functions by removing cells from the target tissue in a scraping fashion. Each strut 188 in this implementation has one collection member 192 coupled to or integral with the strut 188 at or near the distal end of the strut 188. Alternatively, the number of collection members 192 can range from one to ten. In a further alternative, the number of collection members 192 can be any number that can be positioned on a strut 188.

Each strut 188 in this specific embodiment is a beam or rib-like structure 188 with a substantially rectangular cross-section. In one embodiment, the struts 188 are made of polypropylene. Alternatively, the struts 188 can be made of any biocompatible polymer having deformable or flexible characteristics. In a further alternative, the struts 188 can be made of any deformable material for a medical device that returns to its original shape/position.

In one embodiment, each strut 188 is coupled to the proximal base 186 via a hinge (not shown) or other mechanical connection similar to those discussed above with respect to the previous embodiments.

In this implementation, the proximal base 186 also serves as the proximal cap 186 as best shown in FIGS. 4A and 4B. Alternatively, the proximal base 186 and the proximal cap can be separate components. The cap 186 has a round configuration as best shown in FIGS. 4A and 4B that is part of the capsular shape of the body 182. In this embodiment, a catheter tube 196 is positioned through an opening 198 defined in the cap 190 as best shown in FIG. 4B.

One embodiment of an imaging section 200 and an outer shell 202 is depicted in FIGS. 4A and 4C. The imaging section 200 has a base 204, an imaging component (not shown), and a transparent cover 206 that is disposed over and encloses the imaging component (not shown). The imaging component (not shown) can be any imaging component described above in relation to the other embodiments herein. According to certain implementations, the imaging section 200 can also have a lighting component (not shown). In one embodiment, the lighting component (not shown) can be similar to the lighting component 70 discussed above. In use, the imaging section 200 allows for the imaging component (not shown) to capture images of areas distal to the imaging section 200 through the transparent cover 206.

In one implementation, the outer shell 202 has a channel 210 defined in an outer surface of the shell 202 in which a camera wire (not shown) or other power and/or communication wires or cords can be positioned. Thus, a wire (not shown) can be coupled at one end to the imaging component (not shown) in the imaging section 200 and extend proximally from the imaging section 200 along the channel 210.

The catheter tube 196 having an inflatable balloon (not shown) is positioned through the opening 198 in the cap 190 and extends distally therefrom such that the balloon (not shown) is positioned within the outer shell 202 when the shell 202 has been coupled to or is integral with the inner component 184. The balloon (not shown) is in fluid communication with a lumen (not shown) of the tube 196 such that the balloon (not shown) can be inflated via the tube 196. At least one communication line and at least one power line can be coupled to the imaging component (not shown) via the tube 196.

The outer shell 202, according to one implementation, can be coupled to or integral with the inner component 184 to form the outer portion of the device body 182, as best shown in FIG. 4A. The shell 202 in the depicted embodiment has several slots or openings 208 defined therein such that when the shell 202 is disposed over the inner component 184, the collection members 192 and the slots 208 can be aligned such that the collection members 192 extend out of the slots 208 when the collection members 192 are in the deployed position.

In use, the various device embodiments herein provide for imaging and cell collection without the need for sedation or a technically trained practitioner. That is, procedures utilizing the devices disclosed or contemplated herein can be performed by a medical technician, nurse, or other non-specialist on a lucid patient, potentially in an outpatient setting. Further, the deployable brush components of the various embodiments herein eliminate the need for local tissue dissections, thereby reducing complications related to such dissections.

According to certain implementations, the various device implementations disclose or contemplated herein can view, collect, and isolate cell samples from the human esophagus and/or stomach that can aid in the diagnosis of esophageal or stomach diseases including cancer and identify preventable and treatable conditions of the esophagus or stomach. Each embodiment has an imaging component to navigate to the region of interest and locate the cell collection area based on visual characteristics of the target surface, and a cytology component to collect cell samples from the desired location for analysis.

According to one embodiment, the various device and system embodiments disclosed herein can be used in the following manner to detect and/or diagnose various esophageal and/or stomach conditions, including various types of cancer such as esophageal cancer or cardia cancer.

Figure 5A:
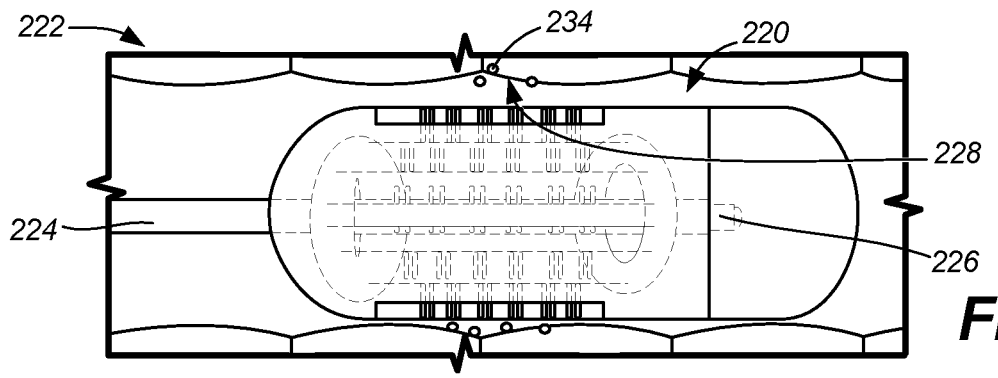
FIG. 5A is a schematic view of an imaging and collection device positioned in an esophagus, according to one embodiment.

A dual-function device 220 according to any of the embodiments disclosed or contemplated herein is inserted into the esophagus 222 as shown in FIG. 5A. According to certain embodiments, the device 220 is swallowed by the patient and then urged distally further into the esophagus 222 by a user urging the proximal portion of the catheter tube 224 (which extends proximally out of the patient's mouth) distally. Because the tube 224 is coupled to the device body 221, urging the tube distally causes the body 221 to be urged distally, thereby allowing for the positioning of the body 221 in the desired location in the esophagus or stomach. The user can track the status and position of the device body 221 via the images captured by the imaging component 226 that are transmitted to a display screen outside the patient's body.

Figure 5B:
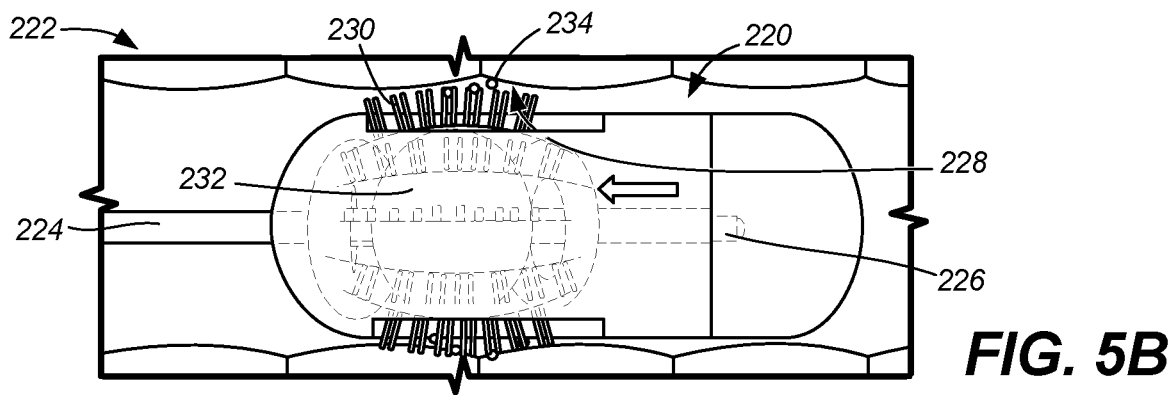
FIG. 5B is a schematic view of the device of FIG. 5A in which the balloon has been inflated.

Once the device 220 is positioned in the desired location such that the brushes (or, in other embodiments, collection members) 230 are positioned adjacent to the target surface 228 of the esophagus (or stomach), the brushes (or collection members) 230 can be deployed. That is, the user can actuate an external actuator (not shown) to pump fluid through the catheter tube 224 and into the balloon 232 to cause the balloon 232 to expand, thereby urging the brushes 230 to move into their deployed position as shown in FIG. 5B. In one embodiment, the external actuator (not shown) is a bulb that is operably coupled to the catheter tube 224 such that squeezing the bulb (not shown) causes fluid to be pumped to the balloon 232. It is understood that while this particular device 220 as shown has brushes 230, other implementations having collection members (such as collection members 192 discussed above) can operate in substantially the same way as the device 220 discussed herein.

Figure 5C:
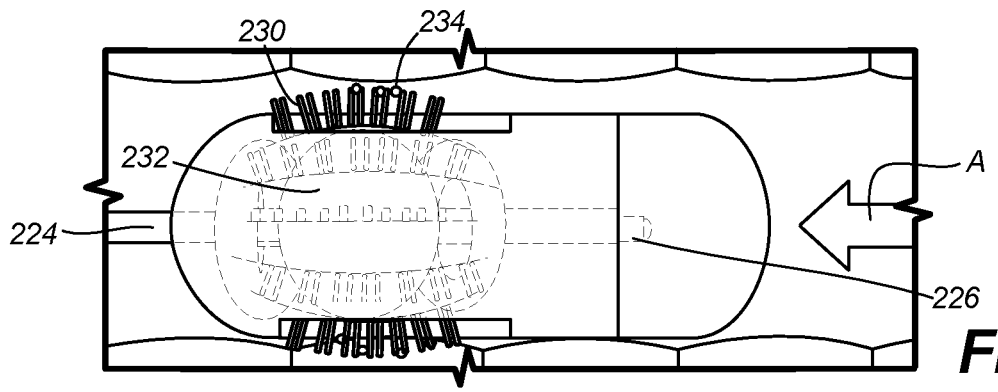
FIG. 5C is a schematic view of the device of FIG. 5A being moved within the esophagus.

Once the brushes 230 are deployed, the device 220 can be urged proximally by the user as best shown in FIG. 5C (as indicated by the arrow A), thereby causing the brushes 230 to scrape or otherwise contact the target surface 228 as the device 220 moves proximally, thereby causing some target cells 234 to adhere to the brushes 230.

Figure 5D:
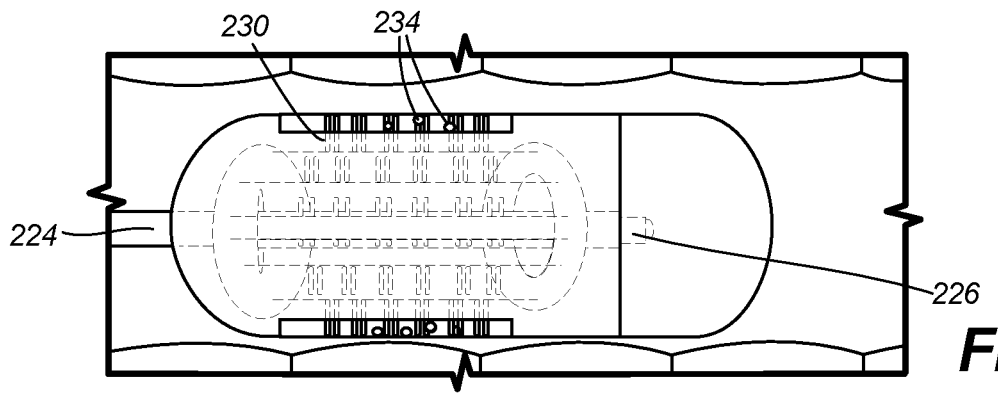
FIG. 5D is a schematic view of the device of FIG. 5A in which the balloon is deflated.

After the device 220 has been urged proximally, the user causes the balloon 232 to deflate. In one embodiment, this is accomplished by releasing the squeeze bulb (not shown). Alternatively, the balloon 232 is deflated in any known fashion. The deflation of the balloon 232 causes the brushes 230 to retract into their undeployed position as shown in FIG. 5D. Because the target cells 234 are adhered to the brushes 230, the cells 234 are retracted into the device 220 with the brushes, thereby resulting in the collection of those cells 234 as depicted in the figure.

Once the brushes 230 have retracted with the collected cells 234, the user can urge the catheter tube proximally, thereby urging the device 220 proximally until it exits the patient's esophagus and mouth. The collected cells can then be tested for one or more esophageal or stomach conditions. If it is determined that a specific condition exists, such as, for example, Barret's esophagus or cancer, then the condition can be treated. In some cases, the early treatment can result in curing or extending the survival rate of the condition.

Figure 6A:
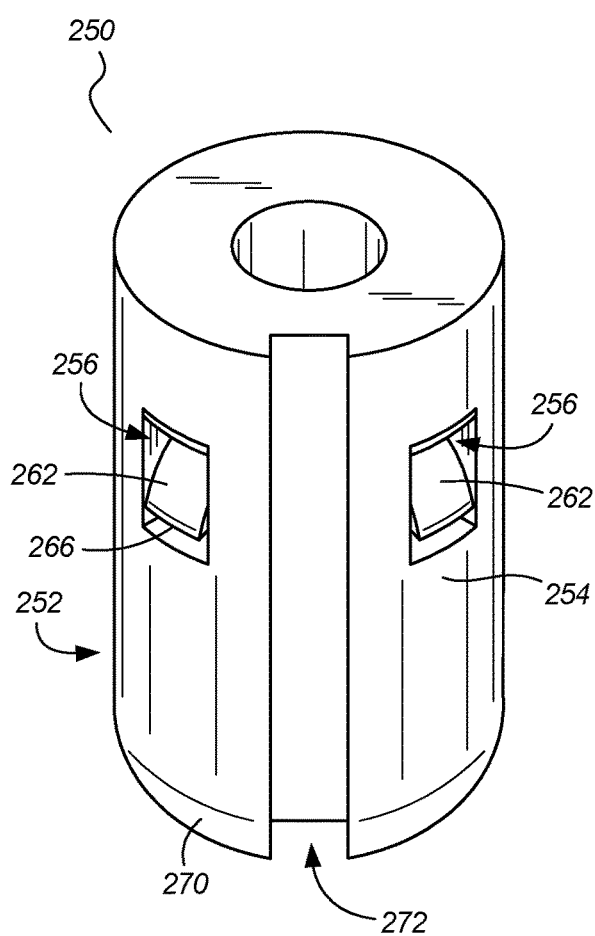
FIG. 6A is a perspective view of an imaging and collection device body, according to a further embodiment.
Figure 6B:
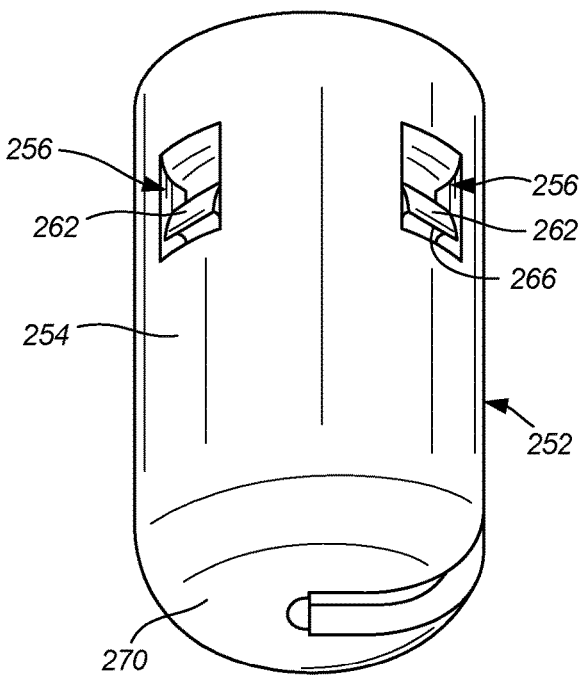
FIG. 6B is another perspective view of the imaging and collection device body of FIG. 6A.
Figure 6C:
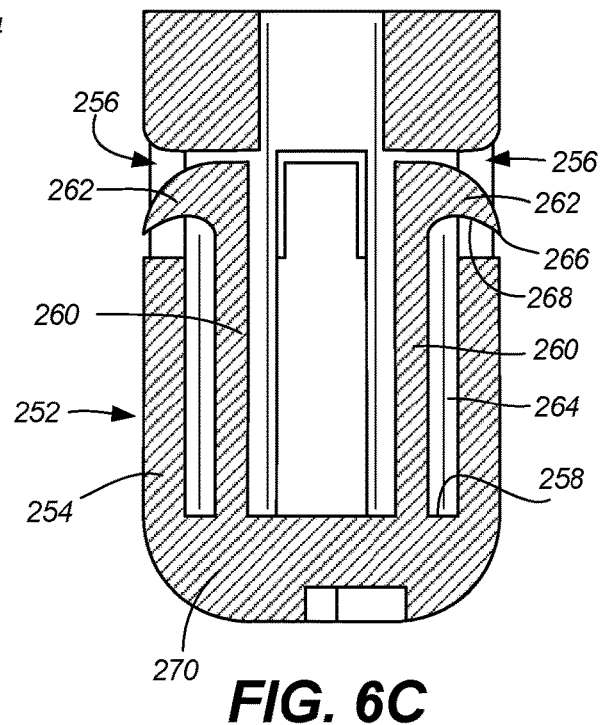
FIG. 6C is a cross-sectional side view of the imaging and collection device body of FIG. 6A.

Another implementation of a dual-function device 250 is depicted in FIGS. 6A-6C. In this embodiment, the device 250 has a body 252 with openings 256 defined in an outer shell 254 of the body 252 as shown. In one embodiment, except as discussed herein, the device 250 has components substantially similar to the components of the dual-function device 180 discussed in detail above. For example, the device 250 has the same or similar imaging-related components and features as the device 180, including, but not limited to, an imaging section (not shown) with a base (not shown), an imaging component (not shown), and a transparent cover (not shown) that is disposed over and encloses the imaging component (not shown) therein.

As best shown in FIG. 6C, the device 250 has a set of collection member deployment struts 260 disposed within the body 252 and extending distally from a base 258 of the body 252. The struts 260 have several collection members 262 coupled thereto. Further, the struts 260 are positioned in the body 252 such that there is a space 264 defined between each strut 260 and the interior wall of the outer shell 254. According to the embodiment as shown, the device 250 has four struts 260, each having a collection member 262. Alternatively, the number of struts 260 can range from two to ten. In a further alternative, the number of struts 260 can be any number that can be positioned within the body 252 and coupled to the base 258, while having collection members 262 coupled thereto. In this embodiment, each strut 260 has a collection member 262 instead of one or more brushes.

In this implementation, each collection member 262 is a scraper-shaped blade 262 with a straight blade edge 266 and a curved face 268 of the blade 262 as best shown in FIG. 6C. The combination of the blade edge 266 and the curved face 268 allows for the capture of cells when the collection members 262 are deployed in a fashion similar to the brushes in other embodiments discussed elsewhere herein. That is, the collection member 262 is urged radially out of the opening 256 such that the blade 262 contacts the target surface and causes target cells to be scraped (or otherwise collected) from the surface by the blade edge 266. As the cells collect on the blade edge 266, they are urged along the curved face 268 of the blade 262 and into the space 264 in the body 252. In one embodiment, each collection member 262 can be referred to as a "scraper" 262 because it functions by removing cells from the target tissue in a scraping fashion.

Each strut 260 in this implementation has one collection member 262 coupled to or integral with the strut 260 at or near the distal end of the strut 260. Alternatively, the number of collection members 262 can range from one to ten. In a further alternative, the number of collection members 262 can be any number that can be positioned on a strut 260. Each strut 260 in this specific embodiment can have substantially similar structures and/or features as the struts 188 discussed above. In one embodiment, each strut 260 is coupled to the proximal base 258 via a hinge (not shown) or other mechanical connection similar to those discussed above with respect to the previous embodiments.

In this implementation, the proximal base 258 can also serve as the proximal cap 258. Alternatively, the proximal base 258 and the proximal cap 270 can be separate components. The cap 270 has a round configuration that is part of the capsular shape of the body 252. In this embodiment, a catheter tube (not shown) can be positioned through an opening (not shown) defined in the cap 270 in a fashion similar to embodiments discussed above.

In one implementation as best shown in FIG. 6A, the outer shell 254 has a channel 272 defined in an outer surface of the shell 254 in which a camera wire (not shown) or other power and/or communication wires or cords can be positioned. Thus, a wire (not shown) can be coupled at one end to the imaging component (not shown) in the imaging section (not shown) and extend proximally from the imaging section (not shown) along the channel 272.

As in previous embodiments, the catheter tube (not shown) having an inflatable balloon (not shown) is positioned through the opening (not shown) in the cap 270 and extends distally therefrom such that the balloon (not shown) is positioned within the body 252. The balloon (not shown) is in fluid communication with a lumen (not shown) of the tube (not shown) such that the balloon (not shown) can be inflated via the tube (not shown). At least one communication line and at least one power line can be coupled to the imaging component (not shown) via the tube (not shown).

As in previous embodiments discussed above, the outer shell 254, according to one implementation, can be coupled to or integral with an inner component (not shown) to form the outer portion of the device body 252. The shell 254 in the depicted embodiment has the openings 256 defined therein such that when the shell 254 is disposed over the inner component (not shown), the collection members 262 and the openings 256 can be aligned such that the collection members 262 extend out of the openings 256 when the collection members 262 are in the deployed position. Alternatively, the outer shell 254 and the inner component (not shown) are one integral component as shown.

Another implementation of a dual-function device 300 is depicted in FIGS. 7A-7G. In this embodiment, the device 300 has an inner (or core) component 304 that is positioned within the body 302 and has a proximal base 306 and a set of collection member deployment struts 308 extending distally from the base 306. As best shown in FIG. 4B, each strut 308 has a collection member 310 coupled thereto.

Figure 7F:
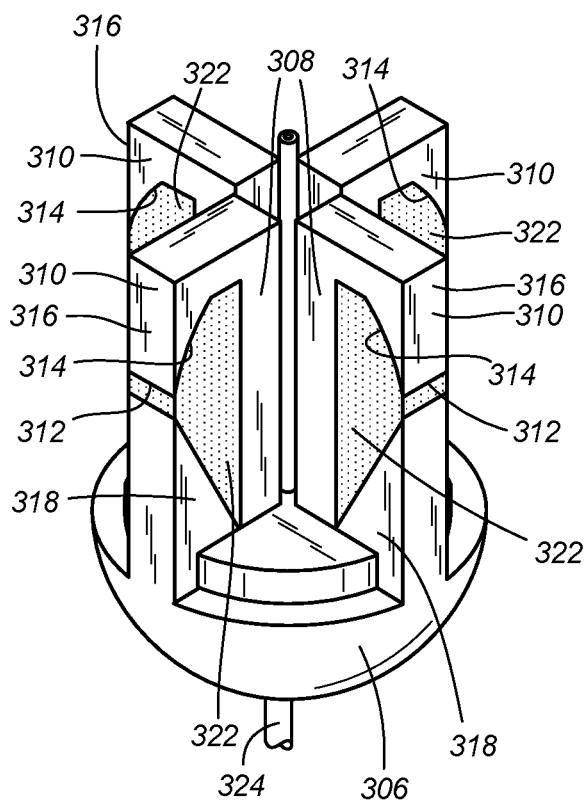
FIG. 7F is a perspective view of the inner component of FIG. 7C with porous inserts, according to one embodiment.
Figure 7G:
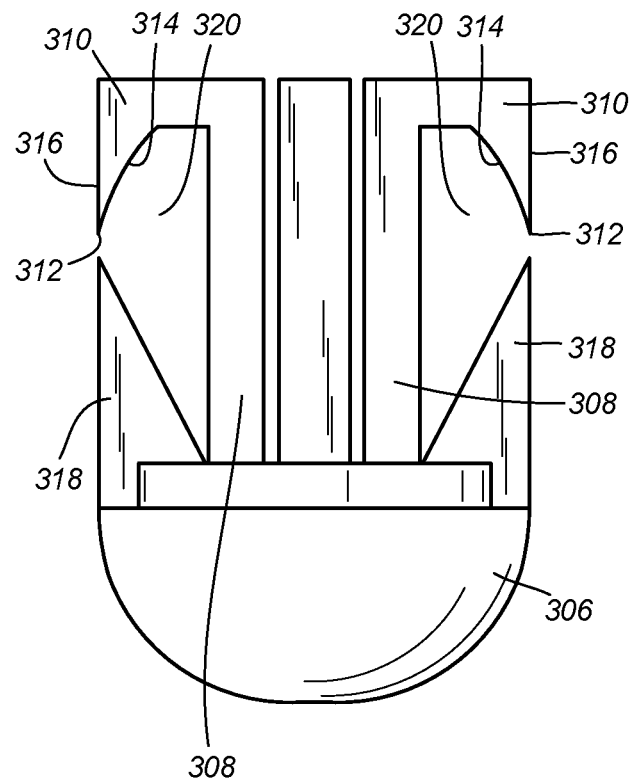
FIG. 7G is a cross-sectional side view of the inner component of FIG. 7C, according to one embodiment.

In one embodiment as best shown in FIG. 7C, the inner component 304 has four struts 308 coupled to and extending from the proximal base 306. Alternatively, the number of struts 308 can range from two to ten. In a further alternative, the number of struts 308 can be any number that can be coupled to the base 306, while having collection members 310 coupled thereto. In this embodiment, each strut 308 has a collection member 310 instead of one or more brushes. In this implementation, each collection member 310 is a scraper-shaped blade 310 with a straight blade edge 312, a curved inner face 314, and a flat outer face 316, as best shown in FIGS. 7C, 7F, and 7G. Further, every strut 308 and collection member 310 pair also has a stationary structure 318 coupled to the proximal base 306 as best shown in FIGS. 7C, 7F, and 7G. The combination of the blade edge 312 and the curved face 314 allows for the capture of cells when the collection members 310 are deployed in a fashion similar to the brushes in other embodiments discussed elsewhere herein. That is, the strut 308 is urged radially into the space 320 defined between the strut 308 and the stationary structure 318 (as best shown in FIG. 7G) such that the collection member 310 is urged radially (while the stationary structure 318 remains stationary) such that the blade 310 contacts the target surface and causes target cells to be scraped (or otherwise collected) from the surface by the blade edge 312. As the cells collect on the blade edge 312, they are urged along the curved inner face 314 of the blade 310 and into the space 320 in the body 252. In one embodiment, each collection member 310 is referred to as a "scraper" 310 because it functions by removing cells from the target tissue in a scraping fashion. Each strut 308 in this implementation has one collection member 310 coupled to or integral with the strut 308 at or near the distal end of the strut 308. Alternatively, the number of collection members 310 can range from one to ten. In a further alternative, the number of collection members 310 can be any number that can be positioned on a strut 308.

Each strut 308 in this specific embodiment is a beam or rib-like structure 308 with a substantially rectangular cross-section. In one embodiment, the struts 308 are made of polypropylene. Alternatively, the struts 308 can be made of any biocompatible polymer having deformable or flexible characteristics. In a further alternative, the struts 308 can be made of any deformable material for a medical device that returns to its original shape/position.

In one embodiment, each strut 308 is coupled to the proximal base 306 via a hinge (not shown) or other mechanical connection similar to those discussed above with respect to the previous embodiments.

According to one alternative embodiment as best shown in FIGS. 7E and 7F, each strut 308 and collection member 310 pair can have a porous material insert 322 disposed in the space 320 defined therebetween. The porous material insert 322 can be made of a sponge-like foam or any other known porous material that can serve to collect the target cells scraped from the target tissue by the blade 310. In certain embodiments, the porous material inserts 322 are removable from the device 300. Alternatively, the porous material inserts 322 are not removable. In a further embodiment, no inserts 322 are incorporated into the device 300.

In this implementation, the proximal base 306 also serves as the proximal cap 306 as best shown in FIGS. 7C, 7F, and 7G. Alternatively, the proximal base 306 and the proximal cap can be separate components. The cap 306 has a round configuration that is part of the capsular shape of the body 302. In this embodiment, a catheter tube 324 is positioned through an opening (not shown) defined in the cap 306 as best shown in FIG. 4B.

One embodiment of an imaging section 330 and an outer shell 332 is depicted in FIGS. 7A and 7B. The imaging section 330 has a base 334, an imaging component (not shown), and a transparent cover 336 that is disposed over and encloses the imaging component (not shown). The imaging component (not shown) can be any imaging component described above in relation to the other embodiments herein. According to certain implementations, the imaging section 330 can also have a lighting component (not shown). In one embodiment, the lighting component (not shown) can be similar to the lighting component 70 discussed above. In use, the imaging section 330 allows for the imaging component (not shown) to capture images of areas distal to the imaging section 330 through the transparent cover 336.

In one implementation, the outer shell 332 has a channel 340 defined in an outer surface of the shell 332 in which a camera wire (not shown) or other power and/or communication wires or cords can be positioned. Thus, a wire (not shown) can be coupled at one end to the imaging component (not shown) in the imaging section 330 and extend proximally from the imaging section 330 along the channel 340.

The catheter tube 324 having an inflatable balloon 350 as depicted in FIG. 7D is positioned through the opening (not shown) in the cap 306 and extends distally therefrom such that the balloon (not shown) is positioned within the outer shell 332 when the shell 332 has been coupled to or is integral with the inner component 304. More specifically, the balloon 350 can be disposed in a space 352 defined by the four struts 308 as best depicted in FIG. 7C. The balloon (not shown) is in fluid communication with a lumen (not shown) of the tube 324 such that the balloon (not shown) can be inflated via the tube 324. At least one communication line and at least one power line can be coupled to the imaging component (not shown) via the tube 324.

The outer shell 332, according to one implementation, can be coupled to or integral with the inner component 304 to form the outer portion of the device body 302 in combination with the collection members 310 and the stationary structures 318, as best shown in FIGS. 7A and 7B. The shell 332 in the depicted embodiment has several slots or openings 354 defined therein such that when the shell 332 is disposed over the inner component 304, the collection members 310 and the stationary structures 318 can be aligned with the slots slots 354 such that the outer surfaces 316 of the collection members 310 and the stationary structures 318 form a portion of the outer portion of the device body 302 and further such that the collection members 310 can extend out of the slots 354 when the collection members 310 are in the deployed position.

It is understood that any of the deployment structures—including struts, rods, etc.—according to any of the embodiments disclosed or contemplated herein can be, in certain implementations, be tensioned when urged out of their undeployed configurations such that the deployment structures are at rest when in their undeployed configurations but are urged toward their undeployed configurations whenever they are urged by the expansion components toward or into the deployed configurations. In other words, each of the deployment structures as disclosed or contemplated herein is at rest when in its undeployed configuration but is tensioned to be urged toward the undeployed configuration whenever it is urged by an outside force (the expansion component) away from the undeployed configuration. For example, as mentioned above, the deployment structures (such as struts 36, for example) that are made of some biocompatible polymer having deformable or flexible characteristics can have elastic characteristics that cause it to return to its original shape/position that result in the structures being urged back toward the undeployed configuration. Further, in certain embodiments in which each deployment structure has a hinge coupling the structure to the device (such as the hinges 44 on struts 36 as discussed above), the hinge can be tensioned to urge the structure back toward its undeployed configuration. As such, no outside force is necessary to cause any deployment structure to move back toward or into its undeployed configuration. Thus, during use, the expansion component is used to urge each deployment structure toward the deployed configuration and the contraction of the expansion component removes the force being applied to the deployment structure, thereby allowing the structure to return to its undeployed configuration.

Alternatively, a mechanism or component can be coupled to each deployment structure to continuously urge the structure back toward its undeployed configuration. For example, in one embodiment, an elastic mechanism (such as, for example, an elastic band) can be coupled to the structure (or the collection member) that applies a counter force (countering the external force applied by the expansion component) urging the structure back toward the undeployed configuration. It is understood that any known mechanism for accomplishing this counter force can be used.

Although the present invention has been described with reference to preferred embodiments, persons skilled in the art will recognize that changes may be made in form and detail without departing from the spirit and scope of the invention.

What is claimed is:

1. A swallowable capsule comprising:
   (a) a core component;
   (b) a plurality of deployment structures operably coupled to the core component, wherein the deployment structures are configured to move between an undeployed configuration and a deployed configuration;
   (c) at least one collection structure coupled to each of the plurality of deployment structures;
   (d) an expansion component disposed within the core component, wherein expansion of the expansion component urges the plurality of deployment structures toward the deployed configuration;
   (e) an outer casing comprising a plurality of openings corresponding to the plurality of deployment structures, wherein the plurality of openings are configured to receive the at least one collection structures when the deployment structures are disposed in the deployed configuration such that the at least one collection structures protrude out of the openings; and
   (f) an imaging component disposed on the capsule.

2. The swallowable capsule of claim 1, wherein the deployment structures are deployment struts or deployment rods.

3. The swallowable capsule of claim 1, wherein the at least one collection structure is coupled to each of the plurality of deployment structures such that the at least one collection structure extends radially outward from the deployment structure.

4. The swallowable capsule of claim 1, wherein the expansion component is an inflatable balloon.

5. The swallowable capsule of claim 1, further comprising a transparent shell disposed at a distal end of the capsule, wherein the imaging component is disposed therein.

6. The swallowable capsule of claim 1, wherein the at least one collection structure comprises a brush or a collection member comprising an opening.

7. The swallowable capsule of claim 1, wherein each of the plurality of deployment structures is coupled at a proximal end to the core component.

8. The swallowable capsule of claim 1, wherein each of the plurality of deployment structures is coupled at each end to the core component.

9. A swallowable capsule comprising:
   (a) a capsule body comprising an outer casing;
   (b) a plurality of deployment structures disposed within the body, wherein the deployment structures are configured to move between an undeployed configuration and a deployed configuration;

(c) at least one collection structure coupled to each of the plurality of deployment structures;
(d) a plurality of openings defined in the outer casing, wherein the plurality of openings correspond to the plurality of deployment structures, wherein the plurality of openings are configured to receive the at least one collection structures when the deployment structures are disposed in the deployed configuration such that the at least one collection structures protrude out of the openings;
(e) an expansion component disposed within the capsule body adjacent to the plurality of deployment structures, wherein expansion of the expansion component causes the plurality of deployment structures to move toward the deployed configuration; and
(f) an imaging component disposed on the capsule body.

10. The swallowable capsule of claim 9, wherein each of the plurality of deployment structures is coupled at a proximal end to an interior portion of the capsule body.

11. The swallowable capsule of claim 10, wherein the at least one collection structure is disposed at a distal end of each of the plurality of deployment structures.

12. The swallowable capsule of claim 9, wherein the at least one collection structure comprises a blade.

13. The swallowable capsule of claim 9, further comprising at least one porous insert positioned adjacent to the at least one collection structure.

14. The swallowable capsule of claim 9, wherein the at least one collection structure is coupled to each of the plurality of deployment structures such that the at least one collection structure extends radially outward from the deployment structure.

15. The swallowable capsule of claim 9, wherein the expansion component is an inflatable balloon.

16. A method of diagnosing a condition of the esophagus or the stomach of a patient, comprising:
positioning a swallowable capsule in the esophagus or stomach of the patient, the swallowable capsule comprising:
(a) a capsule body comprising an outer casing;
(b) a plurality of deployment structures disposed within the body;
(c) at least one collection structure coupled to each of the plurality of deployment structures;
(d) a plurality of openings defined in the outer casing, wherein the plurality of openings correspond to the plurality of deployment structures;
(e) an expansion component disposed within the capsule body adjacent to the plurality of deployment structures; and
(f) an imaging component disposed on the capsule body
collecting cells with the swallowable capsule by expanding the expansion component and thereby urge the plurality of deployment structures into a deployed configuration such that each of the at least one collection structure protrudes through one of the plurality of openings and contacts a target tissue; and
removing the swallowable capsule from the patient.

17. The method of claim 16, further comprising testing the cells to detect the condition after removing the swallowable capsule from the patient.

18. The method of claim 16, further comprising retracting the at least one collection structure by causing the expansion structure to contract and thereby causing the plurality of deployment structures to retract after collecting cells.

19. The method of claim 16, wherein the at least one collection structure comprises a brush, a collection member comprising an opening, or a collection member comprising a blade.

20. The method of claim 16, further comprising capturing images with the imaging component.

* * * * *